United States Patent [19]
Raulston et al.

[11] Patent Number: 5,932,237
[45] Date of Patent: *Aug. 3, 1999

[54] **STEINERNEMA SP. NEMATODE FOR SUPPRESSION OF *HELICOVERPA ZEA* AND *SPODOPTERA FRUGIPERDA***

[75] Inventors: Jimmy R. Raulston, San Bonito, Tex.; Sammy D. Pair, Akoka, Okla.; Cabanillas Enrique, Weslaco, Tex.

[73] Assignee: The United States of America as represented by the Secretary of Agriculture, Washington, D.C.

[*] Notice: This patent is subject to a terminal disclaimer.

[21] Appl. No.: 08/866,676

[22] Filed: May 30, 1997

Related U.S. Application Data

[63] Continuation of application No. 08/439,053, May 11, 1995, Pat. No. 5,674,516, which is a continuation of application No. 07/883,434, May 15, 1992, abandoned.

[51] Int. Cl.⁶ ............................. A01B 79/00; A01C 1/00
[52] U.S. Cl. ............................. 424/405; 47/58; 119/6.7; 800/8
[58] Field of Search ................... 800/2, DIG. 4; 424/405, 406, 407, 48, 409, 93.1, 93.7; 119/6.5, 6.6, 6.7; 47/58

[56] References Cited

U.S. PATENT DOCUMENTS 5,674,516  10/1997  Raulston et al. ..................... 424/405

OTHER PUBLICATIONS

Richter et al. (1990) J. Econ. Entomol. 83(4): 1286–1291.
Bong et al. (1983) J. Econ. Entomol. 76:590–593.
Raulston et al. (1992) J. Econ. Entomol. 85(5): 1666–1670.
Gaugler et al. (1990) in: Entomopathogenic Nematodes in Biological Control, CRC Press, Boca Raton, FL, Table 1, pp. 25–26, 68, 173–191.
Raulston, J.R. et al., "Pupal and Prepupal Parasites of Corn Earworm and Fall Armyworm by Steinernema spp. Under Natural Field Conditions", Abstract, XXVI Congreso Nacional De Entomologia, Vvera Cruz, Mexico, Distributed May 19, 1991, Congress of Entomology, p. 173.
Raulston, J.R., et al. "Parasitismo Del Nematodo Steinernema spp. Sobre Pupas De Gusanos Elotero Y Cogollero Bajo Condiciones De Campo", Abstract, Distributed Oct. 10, 1991, XIV Congreso Nacional De Control Biologico, Buenovista, Mexico, pp., 69–71.
Poinar Jr., George D., et al., *Laboratory Guide to Insect Pathogens and Parasites*, "Nematodes", Plenum Press, New York & London, pp. 235–243.

*Primary Examiner*—Bruce R. Campbell
*Attorney, Agent, or Firm*—M. Howard Silverstein; Randall E. Deck; John D. Fado

[57] ABSTRACT

A novel entomopathogenic nematode of the genus Steinernema, which is effective as a biopesticide for the control of insects, and particularly the corn earworm, *Helicoverpa zea*, and the fall armyworm, *Spodoptera frugiperda*. This nematode has been identified as *Steinernema riobravis*.

30 Claims, No Drawings

STEINERNEMA SP. NEMATODE FOR SUPPRESSION OF *HELICOVERPA ZEA* AND *SPODOPTERA FRUGIPERDA*

This application is a continuation of application Ser. No. 08/439,053, filed May 11, 1995 U.S. Pat. No. 5,674,516 which is a continuation of Ser. No. 07/883,434, filed May 15, 1992, now abandoned.

BACKGROUND OF THE INVENTION

1. Field of the Invention

The corn earworm (CEW), *Helicoverpa zea* (also known as *Heliothis zea*), is a prominent pest of cotton, sorghum, tobacco and numerous vegetable crops, particularly corn, throughout the world.

This invention relates to a novel entomopathogenic nematode of the genus Steinernema, which is effective as a biopesticide for the control of insects, and particularly the corn earworm.

2. Description of the Prior Art

Recent studies have shown that the Lower Rio Grande Valley corn crop is a major source for the production of large populations of the corn earworm and fall armyworm which migrate north to infest corn and other crops of higher cash value such as cotton, tomatoes and soybeans, where they cause severe economic damage [Raulston et al., Production of *Heliothis zea* on Corn in Northeastern Mexico and the Lower Rio Grande Valley of Texas: a Potential Source for Corn and Cotton Infestation on the High Plains of Texas, Proc. Beltwide Cotton Conf., 1986, pp. 222–225, Memphis, National Cotton Council of America; Wolf et al. Phil. Trans. R. Soc. Lond. B 328:619–630, (1990); and Pair et al, Florida Entomologist, 74:200–213, (1991)]. The primary control strategy for the corn earworm is the application of insecticides that result in egg and larval mortality. In Florida and other southeastern states, insecticides are usually applied at least every 48 hours to protect sweet corn during the silking period. However, the corn earworm has given indications of resistance to organochlorine and organophosphate insecticides [Wolfenbarger et al., Bull. Entomol. Soc. Amer., 27:181–185, (1981); and Sparks, Bull. Entomol. Soc. Amer., 27:186–192, (1981)]. This resistance, in addition to the wide public awareness of the environmental damage resulting from chemical pesticides, has increased interest in biological control, and has resulted in the study of a variety of biological control agents. Entomopathogenic nematodes have shown promise as biological control candidates for a number of insect pests.

Nematodes of the genera Steinernema and Heterorhabditis possess most of the characteristics of an ideal biological control agent for insects [Poiner, Taxonomy and Biology of Steinernematidae and Heterorhabditidae,In Gaugler and Kaya (eds.), Entomopathogenic Nematodes in Biological Control, CRC Press, Boca Raton, Fla., (1990), pages 23–61; and Gaugler, J. Nematol., 13:241–249, (1981)]. These nematodes search for their insect hosts; they are highly virulent, killing most hosts within 48 hours; they are easily and inexpensively mass produced; and they have a wide range of insect hosts (Poinar, ibid and Gaugler, ibid). The effectiveness of these nematodes is attributed to a mutualistic bacterium of the genus Xenorhabdus associated therewith [Poinar, ibid]. After entry or penetration of the nematode into the insect host, the bacteria are released from the nematode and rapidly multiply, killing the host insect by septicemia. Conversely, the nematodes protect the bacteria from the environment prior to release within a suitable host.

The pathogenicity of entomopathogenic nematodes to Heliothesis species has been demonstrated previously [Tanada and Reiner, J. Inverteb. Path., 4:139–154, (1962); Bong and Sikorowski, J. Econ. Ent., 76:590–593 (1983); and Howell, J. Inverteb. Path., 33:155–158, (1979)]. However, there exists a negative relationship between larval age and susceptibility to the nematodes [Glazer and Navon, J. Econ. Entomol., 83:1795–1800, (1990); and Samsook and Sikora, Med. Fac. Landbouww. Gent., 46:685–693, (1981)]. Consequently, the use of these nematodes has been against the feeding stages of various insect pests, while their use against prepupal or pupal stages of *H. zea* has been limited.

SUMMARY OF THE INVENTION

We have now discovered a previously unknown entomopathogenic nematode of the genus Steinernema, which is effective as a biopesticide for the control of insects, and particularly the corn earworm, *Helicoverpa zea,* and the fall armyworm, *Spodoptera frugiperda.* This nematode has been identified as *Steinernema riobravis.*

The nematode of this invention has been isolated in pure form from pupae and prepupae of the corn earworm from soil samples of corn fields in the Lower Rio Grande Valley of Texas. When applied to the locus of the target insects, *Steinernema riobravis* will provide improved suppression of the insect population.

In accordance with this discovery, it is an object of this invention to introduce *Steinernema riobravis* as a novel biopesticide for the control of insects. It is also an object of this invention to provide new compositions and methods for controlling insect populations incorporating *Steinernema riobravis.*

A further object of this invention is to provide a biopesticide that is effective against the non-feeding pupal or prepupal stages of insects and that may be applied to the soil.

Another object of this invention is to provide a biopesticide that remains viable at relatively low moisture conditions, is effective for controlling insects in clay soil types, and that provides effective insect control at low inoculum levels.

Yet another object of this invention is to provide a biopesticide for the suppression or elimination of the corn earworm and fall armyworm insects at their source, thereby preventing their movement to other crops.

Other objects and advantages of this invention will become readily apparent from the ensuing description.

DETAILED DESCRIPTION

The entomopathogenic nematode of this invention, *Steinernema riobravis,* is indigenous to the Lower Rio Grande Valley of Texas and northern Tamaulipas, Mexico and may be recovered from corn fields within this geographical area as will be described in more detail hereinbelow. Indeed, over a five year period, 34% of all fields sampled contained corn earworm parasitized with this nematode, and 24.2% contained fall armyworm parasitized with the nematode. Of all corn earworm and fall armyworm prepuae and pupae collected during this study, 11.6% and 9.3%, respectively, were parasitized with the nematode.

The above-mentioned *Steinernema riobravis* has been deposited under the Budapest Treaty in the American Type Culture Collection (ATCC), 12301 Parklawn Drive, Rockville, Md., 20852, USA, on Apr. 1, 1994, and has been assigned accession no. ATCC 75727.

*Steinernema riobravis* n.sp. can be separated from other Steinernema spp. by several characters. Included among the separating traits is the length of the infective juvenile (average length—622 microns; range=561–701 microns). Further the male posterior segment of *S. riobravis* n.sp. lacks a projection or spine of any type which separates it from *Steinernema carpocapsae* and *Steinernema feltiae*. The spicules are generally more curved (a line running parallel with the calomus and lamina forms an angle of 90 to 100 degrees) than those of *S. carpocapsae, S. feltia* and *Steinernema glaseri*. The blunt tip of the spicules on *S. riobravis* n.sp. are distinct from the hooked tip spicules of *S. carpocapsae*. Digestion of genomic DNA with restriction endonucleases generated a unique set of different sized DNA restriction fragments dependent upon the base of the genome sequence. The size distribution of these restriction fragments are different from all known species of nematodes. Morphologically, *S. riobravis* n.sp. resembles *Steinernema intermedia*, however, controlled mating studies indicated that *Steinernema intermedia* n.sp. and *S. intermedia* do not mate with each other.

The nematode described herein is effective for controlling a variety of insects. Without being limited thereto, pests of particular interest known to be susceptible to treatment are agronomically important insects, especially the corn earworm, *H. zea*, and the fall armyworm, *S. frugiperda*. The nematode may be applied for the the control of these agronomically important insects on a number of crops, particularly but not limited to corn, cotton, tomatoes, and soybeans.

production of the nematode may be accomplished using in vivo or in vitro techniques known in the art. As described in the Examples herein, *Steinernema riobravis* may be initially recovered from soil samples taken from corn fields in the Lower Rio Grande Valley of Texas and northern Tamaulipas, Mexico. Following isolation from the environment, the nematodes may then be reared in vivo in susceptible host insects such as *H. zea* prepupae or pupae as illustrated in the Examples. However, in accordance with the preferred embodiment, the nematodes may also be produced on a large scale using in vitro rearing techniques, such as described by Friedman et al. [Mass Production in Liquid Culture of Insect-Killing Nematodes, U.S. Pat. No. 5,023,183, issued Jun. 11, 1991, the contents of which are incorporated by reference herein]. In accordance with either technique, the nematodes may be subsequently harvested and collected in pure or substantially pure form.

Suitable formulations for commercial insecticidal applications would be prepared from nematodes isolated from the environment, particularly in vitro cultivated populations of the nematodes, or pure or substantially pure nematodes. Because of the moisture required by these nematodes for continued viability and infectivity, the nematodes are advantageously applied in combination with a suitable inert carrier or vehicle as known in the art, which carrier is optionally substantially biologically pure. The term "substantially biologically pure inert carrier" is defined herein as an inert carrier having significantly fewer naturally occurring microorganisms relative to the environment. The formulations described herein are storage stable and, depending upon the carrier used, nematode viability can be maintained up to one year with refrigeration.

As a practical matter, to facilitate handling and transport of the biopesticide, and to prevent dessication, the formulations of the nematode and carrier should be enclosed within a closed container such as a drum, jug, flask or plastic bag as is known in the art.

Of particular interest are formulations employing water as a carrier, with a population of the nematodes suspended therein as described in the Examples. In an alternative embodiment the carrier may be a solid phase material or encapsulating agent, upon or within which the nematodes can be immobilized. Suitable carriers of this type include but are not limited to hydrogel agents such as alginate gels, wheat-gluten matrices, starch matrices, wheat-bran bait pellets, clay particles, polyacrylamide gels, or synthetic polymers as are known in the art. Preferred alternative carriers and methods for immobilizing nematodes are described, for example, in Nelsen (U.S. Pat. Nos. 4,753,799; 4,701,326 and 4,615,883 disclosing alginate gels), Connick and Nickle (U.S. patent application Ser. No. 07/560,792, filed Jul. 30, 1990, disclosing wheat gluten), Shasha et al. (U.S. Pat. No. 4,859,377 disclosing starch matrices), and Capinera and Hibbard [J. Agric. Entomol., 4:337–344, (1987) disclosing wheat-bran bait pellets], the contents of each of which are herein incorporated by reference. Formulations of alginate gels containing the nematodes provide the added benefit of enhanced viability after storage, while allowing subsequent conversion to an aqueous liquid by dissolution of the alginate with sodium citrate. When the carrier is other than water, sufficient moisture should be provided to ensure viability and infectivity of the nematodes.

Besides the active agent itself, other additives and adjuncts may be formulated into the compositions of the invention. Examples of these include nutrients, humectants, feeding stimulants (phagostimulants), UV protectants, inert fillers, and dispersants. Humectant materials include but are not limited to glycerol, sugars such as sucrose, invert emulsions, and cellulose ethers.

In use, an insecticidally effective amount of the nematode of this invention is applied to the locus of, or in the vicinity of, the insects to be controlled. An "insecticidally effective amount" is defined herein as that quantity of nematode which will result in a significant mortality rate of a test group of insects compared to an untreated group. The actual effective amount may be readily determined by the practitioner skilled in the art, and may vary with the species of pest, stage of larval development, the type of vehicle or carrier, the period of treatment, environmental conditions (especially moisture), and other related factors. Without being limited thereto, in accordance with the preferred embodiment, the nematodes are applied at a concentration greater than or equal to about $2.5 \times 10^4$ infective juveniles per $m^2$ of soil or field, and especially at a concentration greater than or equal to about $1 \times 10^5$ or $2 \times 10^5$ infective juveniles per $m^2$ of soil or field. Surprisingly, these inoculum levels are six times less than the levels of other entomopathogenic nematodes used to control other soil insect pests [Miller and Bedding, Entomophaga, 27:109–114, (1982). In the alternative, the concentration of nematodes to be applied may also be determined relative to the density of the target insects, if known. The nematodes are preferably applied at a concentration greater than or equal to about 10 infective juveniles per insect, and especially at a concentration greater than or equal to about 100 infective juveniles per insect.

Because of the moisture requirements of these nematodes, and since the soil is their natural habitat and the corn earworm larvae drop to the ground to pupate as part of their life-cycle, techniques wherein the nematodes are applied to the soil are desirable. In accordance with a particular preferred embodiment for use in areas employing irrigation, the nematodes may be admixed with irrigation water prior to or at the time of irrigation, effectively distributing the nematodes across the field. In order to maximize insect kill, the application of the nematodes to the soil should be timed to the exit of prepupae, ensuring the highest rate of parasitism by the nematodes. Best results have been achieved when *Steinernema riobravis* are applied when at least about 10% of the corn earworms have exited the corn ears to pupate, and especially when at least about 50% of the corn earworms have developed into large larvae. Because *Steinernema riobravis* actively seek out and then penetrate and parasitize the target insect pupae and prepupae, feeding by the insect upon the formulation of the nematode is not required. Further, this nematode has the capability of remaining viable and maintaining its infectivity in clay soil types for more than two months after application, providing the added advantage of residual insecticidal activity.

Another technique envisioned for soil application employs encapsulated or pelletized formulations of the nematode. The capsules or pellets containing the nematode may be applied to the soil prior to emergence of the crop, or in the case of corn just prior to larval exit from the corn ear such as by spreading or spraying. Depending upon the carrier selected, the nematodes may be released from the capsules or pellets as they degrade in the soil (Connick and Nickle, ibid) or upon ingestion by the insect. Without being limited thereto, soil application of these encapsulated or pelletized formulations is ideally conducted prior to emergence of the crop or prior to larval exit from the ear.

While soil application techniques are preferred, the formulations of the nematode may also be applied directly upon the crop such as by spraying. Although the nematode may be applied at any time, when corn is to be treated, the nematode is preferably applied while the corn is in the whorl stage. Applying the nematode at this time takes advantage of pockets of moisture retained in whorl folds of the corn because at least some of the nematodes would land within the folds where they would be protected from dissication. Further, the nematodes would still be available to attack and/or be ingested by the target insects on the plant.

EXAMPLE 1

Nematode Extraction and Culture

A previously unknown nematode of the genus Steinernema, subsequently identified as *S. riobravis,* was isolated from soil samples taken from corn plots after harvest. The corn plots were located at the U.S. Department of Agriculture South Farm in Weslaco, Tex.

*H. zea* prepupae were used as trap hosts for this experiment. Approximately 1 kg of a Hidalgo sandy loam soil, was collected at each sample site from the top 10–15 cm of soil. Five prepupae were placed at the bottom of a 30-cm diam ceramic pot, covered with moist soil excavated from the corn plots, and incubated at about 23° C. for 7 d. Dead prepupae were transferred to White traps (White, Science, 66:302–303, 1929) and infective juveniles (IJ) of the nematode were collected 10–14 d after exposure to the soil sample.

The Steinernema nematodes were cultured in vivo in the laboratory using *H. zea* prepupae as a susceptible host. Following harvest the nematodes were suspended in 50 ml of water and stored in 275-ml canted neck Corning tissue culture flasks at 10° C. Nematodes were used for experiments within 1 wk of harvesting.

Helicoverpa Rearing

*H. zea,* was reared in the laboratory on artificial diet following the methods of Raulston & Lingren, the contents of which are incorporated by reference, [Methods for Large-Scale Rearing of Tobacco Budworm, Production Research Report No. 145, ARS, U.S. Dept. of Agriculture, Washington, D.C., 10 pp, 1972] at 29.5° C. Prepupae used in this test were 11 days old and an average weight of 644 mg.

EXAMPLE 2

Infectivity Tests

Dosage mortality trials were performed under laboratory conditions. A 0.5-ml nematode suspension from Example 1 was added to filter paper (Whatman No. 1) contained in a petri dish (60×15 mm). One prepupa of *H. zea* was placed in each of four dishes per treatment, and incubated in the dark, at room temperature (23° C.) for 5 d. Dead insects were individually transferred to White trap dishes (White, ibid) to observe nematode development, evaluate insect mortality, and estimate the number of nematodes developed per insect. Nematodes were collected for identification based on morphological characteristics of the infective juveniles and males (Poinar, ibid).

Dosage mortality tests consisted of seven concentrations: 1, 5, 10, 20, 40, 80 and 100 nematodes per prepupa. Control prepupae were treated with 0.5-ml sterile distilled water alone.

The experiment was designed as a randomized complete block with eight treatments and four plates per treatment; the experiment was repeated five times. The insect mortality data was analyzed by a prohibit procedure using the Statistical Analysis System software (SAS Institute, Cary, N.C., 1988). $Log_{10}$ of the dose value was used in the statistical analysis. LD values and 95% Fiducial limits for nematode concentrations were computed.

Nematode concentrations differentially affected the insect mortality of *H. zea* prepupae ($P=0.0001$). One hundred percent mortality of *H. zea* prepupae was achieved with exposure to 100 IJ per prepupa (Table 1). At this concentration, 60% died in the prepupal stage; however, 40% of the prepupae continued development to the pupal stage prior to nematode-induced death. Doses of 10, 20, 40, and 80 nematodes per *H. zea* prepupa caused mortalities of 40, 55, 85, and 90% respectively. The lowest mortalities (5 and 20%) occurred when prepupae were exposed to only 1 or 5 nematodes per prepupa. The effective dosage required to cause 50% insect mortality ($LD_{50}$) was 13 IJ nematodes (Table 1). The general response of insect mortality (Y) of *H. zea* as a function of nematode concentration (N) per prepupa was estimated by a Probit regression model: Probit $Y=-2.1+ 1.8\ Log_{10}N$ ($P=0.0001$, $df=6$, and $Sy.x=0.078$).

Production of Nematodes

Fourteen days after nematode infection, nematodes were collected by washing the IJ nematodes contained in the "White trap" dishes and those from the filter paper through a 25-mesh screen sieve into a 2,000 ml plastic beaker. Nematodes were extracted from each infected host by transferring a dead insect to a 50-ml plastic centrifuge tube containing about 5 ml water, grinding it with a spatula, and hand stirring on a magnetic mixer for about 1 min. The tube contents were washed through the 25-mesh sieve into the beaker. The total volume was adjusted to 1,000 ml and stirred on a magnetic stir-plate to maintain a homogenous suspension of nematodes. A 1-ml aliquot of the suspension was placed in each of three counting dishes and the average number of nematodes was estimated from counts made under a dissecting microscope.

Production of nematodes per prepupa and pupa cadavers was also affected by the concentration of nematodes to which they were exposed (Table 2). The maximum yield of nematodes/prepupa or pupa occurred at an exposure concentration of 40 IJ nematodes/prepupa. The least yield of nematodes was obtained at an exposure level of 5 nematodes/prepupa. The production of nematodes was not significantly higher on infected prepupae compared to insects that continued development to the pupal stage. The average numbers of nematodes produced per prepupa and pupa cadavers were 325,000 and 310,000 respectively.

EXAMPLE 3

Greenhouse Experiment

The greenhouse experiment was designed to determine the effects of dose and method of Steinernema riobravis application onto the soil on the control of H. zea prepupae. This experiment was conducted at the Subtropical Agriculture Research Laboratory, U.S. Department of Agriculture, Agriculture Research Service in Weslaco, Tex. The soil used in this trial was a clay type (51.2% clay, 35.3% sand, and 13.5% silt, 0.5% organic matter, 7.8 Ph, 39.95 meq/100 g CEC), which was collected from a corn field where this nematode occurs naturally in the soil. The soil was steam-sterilized, sieved through a 9-mesh sieve, and transferred to 15-cm diam clay pots (1175 cc soil/pot). The greenhouse temperature was about 24±3° and 40% relative humidity. Treatments were arranged in a 5×2 factorial with ten treatment combinations of five doses of nematodes (0, 1250, 2500, 5000, and 10,000 nematodes/pot) and two methods of application (soil surface and soil subsurface). The infective juvenile Steinerma riobravis from Example 1 were stored at 10° C. for two wk and applied to the soil at evening time after 1630 hours CST.

For the first method (soil surface), 10 ml of Steinernema riobravis suspended in sterile distilled water from Example 1 was applied to the soil surface previously moistened with 350 ml distilled water. Ten H. zea prepupae were evenly distributed on the soil surface in each pot after nematode application. Each H. zea was contained in inverted 20 ml plastic cups with the bottom open to allow the prepupae to burrow in the soil to pupate. Pots were covered with plastic and small openings (1 mm) were made on the top to reduce evaporation. Five days after nematode treatment, H. zea were carefully extracted from soil, rinsed and transferred to "White" trap dishes (White, ibid) to observe nematode development on dead insects. Evaluation of insect mortality was performed 14 d after nematode treatment based on the development of infective juvenile nematodes from infected H. zea. Nematodes were collected for their identification based on morphological characteristics of infective juveniles and males (Poinar, ibid).

For the second method of application (soil subsurface), the procedure was similar to the first method except that the Steinernema riobravis nematodes were applied to the soil in two parts. Ten ml of nematode aqueous suspension containing half of the nematodes was applied to the soil 2.5 cm deep, then ten H. zea prepupae were placed on the soil in each pot after nematode treatment and covered with the top 2.5 cm moist soil. The second half of the nematodes were applied in 10 ml of sterile distilled water on top of the soil surface. Evaluation of insect mortality was performed as previously mentioned.

The experimental design was a randomized complete block with ten treatments and five replications. An analysis of variance and testing of main effects and interactions was performed on the insect mortality data. Data with zero means were not included in the statistical analysis. The data on percentage insect mortality (Y) were transformed to arcsin $(Y)^{1/2}*57.3$ and their values expressed in degrees. The original data and the transformed data were subjected to an analysis of variance using the General Linear Model (GLM) procedure software of SAS (SAS Institute 1991). The protected least significant difference (LSD, $\underline{P}$=0.05) procedure was used to compare means of doses and methods of nematode application onto the soil to control CEW prepupae in greenhouse.

Inoculum levels and Method of Application of Steinernema

The efficacy of Steinernema riobravis on controlling H. zea prepupae and pupae was influenced by the dose and method used in soil application (Table 3). Since there was a good correspondence in the results of the analysis of variance between the original data and transformed data, the results of the untransformed data are presented. Data contained in these tables were rounded after all the calculations have been performed. The analysis of variance indicated that there were significant differences for both factors dose and method, but their interaction was nonsignificant ($\underline{P}$=0.05). The five doses and two treatment methods were compared using a mean separation procedure as presented in the two-way table of Table 3. Table 3 makes the factorial treatment design explicit and allows all possible pairwise comparisons of these treatments. The main effect dose and method means are compared because there was no significant interaction.

Steinernema riobravis—insect infectivity was a density dependent response. The highest rates of infection were obtained with doses of 10,000 and 5,000 nematodes/pot (555,555 and 277,778 IJ/m$^2$) which resulted in 86 and 68% insect infectivity, respectively. The biocontrol obtained with the highest dose was significantly higher than those obtained at lower inoculum levels, except with rate of 5,000 nematodes/pot ($\underline{P}$=0.01) (Table 3). The application method also influenced the efficacy of Steinernema riobravis in controlling H. zea prepupae and pupae. The subsurface method resulted in 81% mortality which was higher than 45% insect mortality achieved with nematodes applied with the surface method. When nematodes were applied to the soil by the subsurface method at levels of 5,000 and 10,000 IJ/pot, 90 and 98% insect mortality occurred, respectively (Table 3).

EXAMPLE 4

Field Experiments

The field trials were designed to determine the effects of dose and timing of nematode application to the soil on the control of H. zea prepupae and pupae. Five concentrations of Steinernema riobravis from Example 1 (0, 25000, 50000, 100000, and 200000 nematodes/m$^2$) were applied to the soil at three different time schedules relative to the maturity of H. zea larvae infesting the corn ears: 1) when 10% of the H. zea had exited the corn ear to pupate, 2) when 50% of the H. zea had developed to large larvae ($\geq$21 mm), and 3) when 40% of the H. zea had reached medium larvae (20 mm). Corn plantings between fields were separated two weeks from each other. Infective juvenile nematodes stored at 10° C. for 2 wk were suspended in 8 liters of water and applied with a sprinkling can to each plot at evening time (after 1630 hours CST). Control treatments of water were also applied. After nematode application, prepupae and pupae were extracted with a garden trowel by carefully scraping the top 10 cm of a 2-m$^2$ soil sample in each plot, at six days after 95% of the H. zea had left the corn ear to pupate. Each prepupa or pupa was placed individually in a 20 ml plastic cup, kept in a styrofoam box and processed in the laboratory in the same day. Evaluation of insect mortality was based on the presence of *Steinernema riobravis* nematodes from infected *H. zea*, as mentioned in the greenhouse trial of Example 3. The experimental design was a randomized complete block with fifteen treatments and eight replications. The treatments were arranged in a 5×3 factorial, with five levels of nematodes and three times of application already mentioned. Plots were single rows 4 m long by 1 m wide. Each plot was separated 16 m within rows and 2 m between rows. An analysis of variance and testing of the main effects and interactions was performed on the insect mortality data. Data transformation, its analysis and mean separation were performed using the procedures described in the greenhouse trial of Example 3.

Inoculum Levels and Timing of Steinernema

The efficacy of *Steinernema riobravis* was greatly influenced by dose and timing of the control of *H. zea* prepupae and pupae in corn fields (Table 4). The results of untransformed data are presented in Table 4 for reasons previously mentioned. Analysis of variance indicated significant differences for dose and time but no significant differences for their interactions ($P=0.05$). Therefore, the main effect means are compared. Generally, each of these four inoculum levels was significantly greater than the 11% mortality in control plots. Prepupal and pupal infectons were 47, 51, 66, and 72% at application rates of 25000, 50000, 100000 and 200000 Ij/m$^2$ (Table 4). Natural prepupal and pupal infection in the control plots was 11%. The best inoculum level of 200,000 IJ/m$^2$ resulted in 72% insect mortality which was significantly ($P=0.05$) higher than those attained at lower inoculum levels, except with level of 100,000 IJ/m$^2$. The best timing of nematode application occurred when 10% of the *H. zea* had exited the corn ear to pupate or when 50% of the *H. zea* had developed to large larvae. This resulted in 77 and 78% insect mortality, respectively. However, poor control of *H. zea* (22%) resulted from plots that received nematodes when 40% of CEW had reached to medium larvae. The highest mortality was obtained in treatments receiving 200,000 IJ/m$^2$ applied when 10% of the *H. zea* had left the corn ear to pupate or when 50% of the corn earworms had developed to large larvae. This resulted in 95 and 100% of CEW prepupae and pupae infected with Steinernema. Another successful treatment was with dose of 100,000 IJ/m$^2$ applied when 50% of the *H. zea* had developed to large larvae which resulted in 92% infectivity (Table 4).

Residual Efficacy of *Steinernema riobravis*

A laboratory bioassay and two extraction methods were used to determine the residual efficacy and nematode population in soil. The residual efficacy of *Steinernema riobravis* on the control of *H. zea* prepupae was performed using a lab bioassay method (unpublished data). Soil samples were collected from corn plots treated with 200,000 nematodes/m$^2$ as in Example 4 on three different dates. Two soil subsamples were collected with a garden trowel from the 10–15 cm soil surface of the remaining 2 m$^2$ undisturbed soil on each eight plots at each three corn fields. Soil samples were placed in plastic bags, stored in styrofoam boxes and processed in the lab the same day. Composite soil samples were obtained separately from each of the corn fields by gently mixing the soil subsamples. Two aliquants (100 cc soil) were transferred each separately into two assay chambers to detect the presence of *Steinernema riobravis*. Two *H. zea* prepupae were buried in soil contained in each ten chambers per field. Chambers were placed in dark room (25±2° C.) for five days, then the *H. zea* were removed, rinsed and transferred to "White" trap dishes (White, ibid) to detect the presence of infective juveniles at 12 d after *H. zea* were exposed to soil. The residual efficacy of this nematode was estimated by the percentage of Steinernema—dead insects based on the development of infective juveniles in the cadavers of *H. zea*. Infective juveniles started exiting from infected hosts about 10 d after insects were exposed to natural soil. Nematodes were collected for their identification based on morphological features of IJ and males (Poinar, ibid). The residual population of *Steinernema riobravis* in soil was estimated by using the Baermann funnel and the centrifugal flotation (modified) methods described by Barker [Nematode extraction and bioassays. Pp. 19–35. In K. R. Barker, C. C. Carter, and J. N. Sasser, eds. An advanced treatise on Meloidogyne, vol. 2. Methodology. Raleigh: North Carolina State University Graphics, 1985]. Two separate aliquants (100 cc soil) from the composite soil sample of each three corn fields were separately processed by the two extraction methods. Nematodes were collected at 24 and 48 h for the Baermann method. Extracts containing nematodes were counted under a stereoscopic microscope and a 0.5-ml nematode suspension was added to filter paper (Whatman No. 1) contained in petri dishes for assay of infectivity. One *H. zea* prepupae was added to each petri dish (60×15 mm) and incubated in dark room (25±2° C.) for 5 d. Then, each dead insect was transferred to White trap dishes (White, ibid) to verify nematode emergence and its identification. Evaluation of nematode assays were based on numbers of live nematodes per 100 cc soil. In addition to this absolute measure of density, the residual density (Rd) was calculated as a percentage: $Rd=(Rp/Tp)*100$ where Rp=numbers of nematodes of a species in a sample; Tp=total number of nematodes of the same species initially applied to the soil.

Of the two extraction methods, the highest recovery of nematodes from soil was obtained with the Baermann funnel (Table 3). Residual densities of *S. riobravis* extracted with the Baermann funnel were 22, 45 and 28% of the total numbers of nematodes applied to the soil on the three dates, respectively. The residual efficacy of *S. riobravis* as indicated by the laboratory bioassay resulted in 80, 85 and 90% insect mortality from plots that received nematodes 11, 10 and 8 wk after treatment, respectively (Table 5).

EXAMPLE 5

Geographical Distribution

Our research was conducted over 5 consecutive years in an irrigated region that extends about 60 km north from the Rio Grande River into the U.S.A and about 60 km south into Mexico. East to west, the region extends from the cities of Brownsville, Tex. and Matamoros, Tamaulipas, Mexico about 190 km to Camargo, Tamaulipas. This area is located in the semi-arid subtropics and receives approximately 600–700 mm of annual rainfall. Many soil types exist in the area, generally consisting of 25–70% clay, 15–65% sand, 15% silt and a pH>8. About 200,000 ha of irrigated corn are planted annually in this region in February and early March. Fruiting normally begins in early to mid-May and mature corn earworm and fall armyworm larvae exit the corn to pupate in late May and early June. Little or no pesticide is used to control the corn earworm and fall armyworm larvae that infest this crop.

Sampling Procedure

Quantitative estimates of the number of corn earworm and fall armyworm prepupae and pupae parasitized by the indigenous *Steinernema riobravis* in fruiting corn was accomplished by excavating two, 1 m$^2$ soil samples in each of 90–120 fields annually from 1986 to 1990. Samples were taken at 50 and 100 m from field edges after most of the larvae had exited the ear to pupate.

Because the standard row spacing for most corn produced in the region is 100 cm, the surface area for soil sampled extended from the plants of one row to the plants of an adjacent row by 100 cm along the rows. Each sample site was thoroughly searched for corn earworm and fall armyworm prepupae, pupae, and pupal exuviae. Insects were initially exposed by carefully scraping the soil surface with a garden trowel to uncover tunnels leading to the pupae. Following the removal of insects from exposed pupation chambers, soil was then excavated to a depth of 10–15 cm to recover any insects missed in the initial search. All extracted insects were placed individually in 20 ml plastic cups and transported to the laboratory for subsequent determination of species, sex, and developmental stage. All dead pupae were examined with the aid of a dissecting microscope to determine the presence of adult or infective juvenile *S. riobravis*. Mortality was attributed to the nematode only if nematodes were observed in the cadaver. We did not attempt to determine other factors resulting in prepual or pupal mortality.

Depending on the year, sampled fields were located on 5 or 6 transects through the main corn-growing area centered near Rio Bravo, Tamaulipas, Mexico and through the center of the irrigation district on the Texas side of the Rio Grande River. The following transects were common to all years of our study: 1. (west) extended south approximately 25 km from Rio Bravo; 2. (east) located 15 km east of Rio Bravo and extended approximately 25 km south; 3. (south) located 15 km south of Rio Bravo and extended from the west side of the irrigation district east approximately 25 km; 4. (center) located 5 km south of Rio Bravo and extended from the west side of the irrigation district east approximately 25 km; 5. (north) extended from 20 km east of McAllen, Tex. to the east approximately 50 km to Harlingen, Tex. Fields were sampled on an additional transect which extended west from Reynosa to Camargo (ca. 45 km) for two years of the study. From 15 to 20 fields (each separated by ca. 1.5 km) were sampled annually on each transect.

Data analysis

To determine differences in parasitism between species, life stage and year, data were analyzed by analysis of variance and means separation was accomplished by computing Least Square Means and testing the hypothesis, $H_o$: LSM $(_i)$=LSM$(_j)$. Arcsine transformations were performed on all percentage data before analysis.

Averaged over years, significantly more of the sampled fields harbored corn earworm prepupae, pupae or exuviae than fall armyworm (92.6 and 60.2% respectively; df=1,8 F=7.5 P>F=0.0253) (Table 1). Considering only those fields where corn earworm or fall armyworm were found in our samples, 34.2 and 24.2% respectively contained either prepupae or pupae that were parasitized by *Steinernema riobravis*. The highest incidence of fields with parasitized corn earworm or fall armyworm was observed in year 1 (52.5 and 36.4% respectively) while the lowest incidence occurred in year 3 (14.1 and 0% respectively).

The highest incidence of corn earworm and fall armyworm parasitism, totaled across prepupae and pupae (including pupal exuviae), occurred in year 2 (21.3 and 21.2% respectively) while the lowest incidence occurred in year 3 (2.9 and 0% respectively) (Table 7). Although fewer corn earworm prepupae were excavated than pupae and exuviae combined, a significantly higher percentage of the prepupae were parasitized (df=1,645; F=21.47; P>0.0001).

Similarly, a significant higher percentage of fall armyworm prepupae were parasitized compared with pupae (df=1,380; F=17.15; P>0.0001). Averaged over all years, 11.6% and 9.3% of all corn earworm and fall armyworm excavated were parasitized by *Steinernema riobravis* respectively. No significant difference in the parasitism rate between corn earworm and fall armyworm was noted.

Corn earworm and fall armyworm parasitism averaged 27.7% and 29.5% respectively, when calculated using only those corn earworm collected from fields where at least one prepupa or pupa was parasitized (Table 8). Calculated on this basis, the highest rates of parasitism for corn earworm and fall armyworm (45.3% and 84.6% respectively), were observed in year 2. Averaged over years, there was again no significant difference in the percentage of parasitism between corn earworm and fall armyworm.

Significant differences in corn earworm parasitism occurred among transects (Table 9), when comparing those transects that were common to all years of the study. This comparison included all corn earworm or fall armyworm excavated from fields within transects regardless of the presences of *Steinernema riobravis* within individual fields. The highest incidence of corn earworm parasitism (15.4%) was measured in the westernmost transect and the lowest rate of parasitism was observed in the northernmost transect which was located in the U.S.A. There was no significant difference in the rate of parasitism of fall armyworm due to transect location (Table 9).

Considering all prepupae, pupae and pupal exuviae excavated, 23.5% and 20.1% of corn earworm and fall armyworm were dead at the time of collection (Table 10). The highest mortality occurred in year 2 and the lowest in year 5. When corn earworm mortality was partitioned between the prepupal and pupal stages, a significantly higher percentage occurred in the pupal stage (80.6%) (df=1,560; F=372, P>0.0001). Similarly, when fall armyworm mortality was partitioned between prepupae and pupae, a significantly higher percentage occurred in the pupal stage (77.1%) (df=1.262; F=421; P>0.0001). Of those prepupae and pupae that were dead at time of collection, 49.4% and 46.1% of corn earworm and fall armyworm, respectively, contained *Steinernema riobravis* nematodes. The highest percentage of corn earworm and fall armyworm mortality resulting from parasitism (67.5% and 66.1%, respectively) occurred in year 1. Averaged over all years, 49.4% and 46.1% of all corn earworm and fall armyworm mortality, respectively, resulted from *Steinernema riobravis* parasitism. There was no significant difference (P>0.05), in the percentage of nematode induced mortality between the prepupal and pupal stages.

It is understood that the foregoing detailed description is given merely by way of illustration anmd that modification and variations may be made therein without departing from the spirit and scope of the invention.

TABLE 1

Effect of different concentration of *Steinernema riobravis* on the mortality of *Helicoverpa zea* in vitro

| Nematodes added/prepupa | Dead insects[a] | Insect mortality % | Probit[b] LD Value | 95% Fiducial Limits |
|---|---|---|---|---|
| 1 | 1 | 5 | 2 | 1–3 |
| 5 | 4 | 20 | 5 | 2–7 |

TABLE 1-continued

Effect of different concentration of *Steinernema riobravis* on the mortality of *Helicoverpa zea* in vitro

| Nematodes added/prepupa | Dead insects[a] | Insect mortality % | Probit[b] LD Value | 95% Fiducial Limits |
|---|---|---|---|---|
| 10 | 8 | 40 | 10 | 7–13 |
| — | — | 50 | 13 | 9–18 |
| 20 | 11 | 55 | 15 | 11–21 |
| 40 | 17 | 85 | 48 | 33–84 |
| 80 | 18 | 90 | 65 | 43–125 |
| — | — | 95 | 103 | 63–231 |
| 100 | 20 | 100 | — | — |

[a]Based on 20 prepupae.
[b]The $LD_{50}$ and $LD_{95}$ values were computed by Probit analysis and added to this table.

TABLE 2

Numbers of *Steinernema riobravis* nematodes extracted from infected prepupae and pupae of *Helicoverpa zea*

| Nematodes added/prepupa | No. dead Insects[a] | | Average nematodes produced[b] (X 1000) | |
|---|---|---|---|---|
| | Prepupae | Pupae | Per prepupa | Per pupa |
| 1 | 0 | 1 | | |
| 5 | 2 | 2 | 314 (168–460) | 190 (176–204) |
| 10 | 1 | 7 | 336 (336–336) | 317 (200–508) |
| 20 | 7 | 4 | 303 (276–352) | 296 (292–308) |
| 40 | 11 | 6 | 375 (288–552) | 341 (280–452) |
| 80 | 6 | 12 | 257 (200–400) | 304 (296–384) |
| 100 | 12 | 8 | 326 (112–440) | 330 (200–436) |

[a]Based on 20 prepupae.
[b]Range indicated in parenthesis.

TABLE 3

Effects of dose and method of applicaiton of *Steinernema riobravis* onto the soil on the control of *H. zea* prepupae and pupae in greenhouse.

| Nematode applicaiton method | Insect Mortality (%) Dose (No. nematodes/pot) | | | | | |
|---|---|---|---|---|---|---|
| | 0 | 1250 | 2500 | 5000 | 10000 | Mean[a] |
| Subsurface | 0 | 50 | 86 | 90 | 98 | 81 a |
| Soil surface | 0 | 28 | 32 | 46 | 74 | 45 b |
| Mean[a]: | 0 | 39c | 59b | 68ab | 86a | |

[a]Data with zero mean were not included in the analysis. Means followed by a common letter aren ot significantly different.
LSD(Dose) = 19.6; LSD(MEthod) = 13.9; MSE = 466.3; df = 31; (p = 0.05).

TABLE 4

Effects of timing and dose of *Steinernema riobravis* applied to the soil on the control of *H. zea* prepupae and pupae in corn field.

| Nematode application time[a] | Insect Mortality (%) Dose: No. nematodes (X 1000)/$m^2$ | | | | | |
|---|---|---|---|---|---|---|
| | 0 | 25 | 50 | 100 | 200 | Mean[bc] |
| 10% cutouts | 20 | 68 | 68 | 76 | 95 | 77a |
| 50% large larvae | 14 | 43 | 77 | 92 | 100 | 78a |
| 40% medium larvae | 0 | 29 | 8 | 29 | 21 | 22b |
| Mean[c]: | 11c | 47b | 51b | 66ab | 72a | |

[a]Timing nematode application when 10% of CEW had exited the corn ear to pupate (cutouts) and when the corn fields were infested with large or medium larvae.
[b]Data for dose zero were not included in the Time means.
[c]Time and dose means followed by a common letter are not significantly different. LSD(Dose) = 18; LSD(time) = 14; (P = 0.05).

TABLE 5

Residual efficacy of *Steinernema riobravis* against *H. zea* prepupae after nematode application to corn field plots as determined by two extraction methods and a laboratory bioassay.

| Nematode application period | Number of nematodes/100 cc soil | | | | Insect mortality (%) Lab bioassay[b] |
|---|---|---|---|---|---|
| | Baermann funnel | Rd[a] (%) | Centrifugal flotation | Rd (%) | |
| 1 | 43 | 22 | 10 | 5 | 80 |
| 2 | 90 | 45 | 39 | 20 | 85 |
| 3 | 56 | 28 | 26 | 13 | 90 |
| Mean: | 63 | 32 | 25 | 13 | 85 |

[a]Rd, residual density of nematodes is the ratio of the number of nematodes extracted to total number of nematodes initially applied to the soil (200 IJ/100 cc soil).
[b]Based on 20 *H. zea* prepupae.

TABLE 6

Percentage of corn fields in Lower Rio Grande Valley where excavated corn earworn amd fall armyworm were parasitized by *Steinernema riobravis*.

| Year | Number fields sampled | Number fields with | | Percent fields with parasitized[a] | |
|---|---|---|---|---|---|
| | | cew | faw | cew | faw[b] |
| 1 | 120 | 118 | 99 | 52.5 | 36.4 |
| 2 | 105 | 83 | 37 | 37.4 | 21.6 |
| 3 | 90 | 85 | 17 | 14.1 | 0.0 |
| 4 | 100 | 99 | 87 | 28.3 | 26.6 |
| 5 | 100 | 92 | 70 | 30.4 | 11.4 |
| Total | 515 | 477 | 310 | | |
| Average | | | | 34.2 | 24.2 |

[a]Based on fields where pupae were collected from soil samples.
[b]cew = *H. zea*; faw = *S. frugiperda*

TABLE 7

Incidence of *H. zea* and *S. frugiperda* prepupae and pupae parasitism by *Steinernema riobravis* in corn fields in the Lower Rio Grande Valley.

| | Percent parasitized[a] | | | | | |
|---|---|---|---|---|---|---|
| | prepupae | | pupae | | total[b] | |
| Year | cew | faw | cew | faw | cew | faw[c] |
| 1 | 49.1(57) | 74.4(39) | 17.7(813) | 15.7(549) | 19.8a | 19.6a |
| 2 | 25.0(20) | 60.0(5) | 21.0(205) | 19.1(47) | 21.3a | 21.2a |
| 3 | 4.5(88) | 0.0(5) | 2.6(431) | 0.0(26) | 2.9bc | 0.0c |
| 4 | 11.0(82) | 2.3(177) | 7.0(740) | 3.6(754) | 7.4bc | 3.3b |

TABLE 7-continued

Incidence of *H. zea* and *S. frugiperda* prepupae and pupae parasitism by *Steinernema riobravis* in corn fields in the Lower Rio Grande Valley.

| | Percent parasitized[a] | | | | | |
|---|---|---|---|---|---|---|
| | prepupae | | pupae | | total[b] | |
| Year | cew | faw | cew | faw | cew | faw[c] |
| 5 | 18.0(61) | 14.3(7) | 8.3(539) | 4.7(193) | 9.3b | 5.0b |
| Avg. | 18.5 | 15.5 | 10.8 | 8.3 | 11.6 | 9.3 |

[a]Numbers in parenthesis indicate number of insects observed.
[b]Column values followed by the same letter are not significantly different (p < .05) as determined by Least-squares means.
[c]cew = *H. zea*; faw = *S. frugiperda*

TABLE 8

Frequency of *H. zea* and *S. frugiperda* parasitism by *Steinernema riobravis* in fruiting corn fields where at least one parasitized prepupae or pupae was excavated.

| | Number fields | | Number insects excavated | | Percent parasitized[a] | |
|---|---|---|---|---|---|---|
| Year | cew | faw | cew | faw | cew | faw |
| 1 | 62 | 36 | 549 | 316 | 32.1b | 37.6c |
| 2 | 31 | 8 | 115 | 13 | 45.3a | 84.6a |
| 3 | 12 | 0 | 87 | 0 | 17.9b | — |
| 4 | 28 | 11 | 334 | 407 | 19.6c | 13.7c |
| 5 | 28 | 8 | 243 | 21 | 23.8bc | 47.6b |
| Total | 161 | 63 | 1328 | 757 | | |
| Average | | | | | 27.7 | 29.5 |

[a]Column values followed by the same letter are not significantly different (p < .05) as determined by Least-squares means.
[b]cew = corn earworm; faw = fall armyworm

We claim:

1. A method for controlling insects comprising applying to a locus of said insects an insecticidally effective amount of entomopathogenic *Steinernema riobravis* American Type Culture Collection accession number 75727 or progeny thereof, and which is isolated from the environment, said *Steinernema riobravis* being insecticidally effective against said insects.

2. The method as described in claim 1 wherein said insects are corn earworms *Helicoverpa zea*.

3. The method as described in claim 1 wherein said insects are fall armyworms *Spodoptera frugiperda*.

4. The method as described in claim 1 wherein said *Steinernema riobravis* are in a suspension in water and said step of applying comprises spraying said suspension.

5. The method as described in claim 1 wherein said step of applying comprises applying said *Steinernema riobravis* to soil.

6. The method as described in claim 5 wherein said *Steinernema riobravis* are applied at a concentration greater than or equal to $2.5 \times 10^4$ infective juveniles of said *Steinernema riobravis* per m$^2$ of soil.

7. The method as described in claim 6 wherein said *Steinernema riobravis* are applied at a concentration greater than or equal to $1 \times 10^5$ infective juveniles of said *Steinernema riobravis* per m$^2$ of soil.

8. The method as described in claim 5 wherein said *Steinernema riobravis* are in a suspension in water and said step of applying comprises admixing said suspension with irrigation water and irrigating said soil with the admixture.

9. The method as described in claim 1 wherein said *Steinernema riobravis* are applied at a concentration greater than or equal to 10 infective juveniles of said *Steinernema riobravis* per insect.

10. The method as described in claim 9 wherein said *Steinernema riobravis* are applied at a concentration greater than or equal to 100 infective juveniles of said *Steinernema riobravis* per insect.

11. The method as described in claim 1 wherein said step of applying comprises applying said *Steinernema riobravis* to insect pupae or prepupae in soil.

12. The method as described in claim 1 wherein said insects are the corn earworm *Helicoverpa zea* and said step of applying comprises applying said *Steinernema riobravis* onto corn fields infested with said corn earworms.

13. The method as described in claim 12 wherein said *Steinernema riobravis* are applied when about 10% or more of the corn earworms have exited the corn ears to pupate.

14. The method as described in claim 12 wherein said *Steinernema riobravis* are applied when about 50% or more of the corn earworms have developed into large larvae.

15. The method as described in claim 1 wherein said *Steinernema riobravis* are substantially pure.

16. The method as described in claim 1 wherein said *Steinernema riobravis* are in pure form.

17. The method as described in claim 1 wherein said *Steinernema riobravis* are applied in combination with an inert carrier.

18. The method as described in claim 17 wherein said carrier is substantially biologically pure.

19. The method as described in claim 17 wherein said carrier is a solid phase material and said *Steinernema riobravis* are immobilized on or within said carrier.

20. The method as described in claim 19 wherein said carrier comprises a hydrogel agent.

21. The method as described in claim 20 wherein said hydrogel agent comprises alginate.

22. The method as described in claim 17 further wherein said *Steinernema riobravis* are applied in combination with a humectant.

23. The method as described in claim 17 wherein said carrier comprises an encapsulating agent and said *Steinernema riobravis* are encapsulated within said agent.

24. The method as described in claim 22 wherein said humectant is selected from the group consisting of glycerol, sugars, invert emulsions, and cellulose ethers.

25. The method as described in claim 1 wherein said *Steinernema riobravis* are applied to the soil in the locus of said insects.

26. The method as described in claim 1 wherein said *Steinernema riobravis* are applied to plants in the locus of said insects.

27. The method as described in claim 5 wherein said *Steinernema riobravis* are applied at a concentration of about $2.5 \times 10^4$ infective juveniles of said *Steinernema riobravis* per m$^2$ of soil.

28. The method as described in claim 6 wherein said *Steinernema riobravis* are applied at a concentration of about $1 \times 10^5$ infective juveniles of said *Steinernema riobravis* per m$^2$ of soil.

29. The method as described in claim 1 wherein said *Steinernema riobravis* are applied at a concentration of about 10 infective juveniles of said *Steinernema riobravis* per insect.

30. The method as described in claim 9 wherein said *Steinernema riobravis* are applied at a concentration of about 100 infective juveniles of said *Steinernema riobravis* per insect.

* * * * *